US00PP34509P2

(12) United States Plant Patent
Hansen

(10) Patent No.: US PP34,509 P2
(45) Date of Patent: Aug. 16, 2022

(54) ***PANICUM* PLANT NAMED 'NIAGARA FALLS'**

(50) Latin Name: ***Panicum virgatum* (L.)**
Varietal Denomination: 'Niagara Falls'

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,300

(22) Filed: Apr. 28, 2022

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Karen M Redden

(57) ABSTRACT

A new and distinct plant of ornamental Switch Grass named *Panicum* 'Niagara Falls' with wide, blue-green, broadly-arching foliage that retains its coloration into the fall. The upright and dense culms produce medium-height plants with broadly-spreading airy panicles beginning greyed reddish-purple and becoming tan seed heads that are retained into winter. The broadly-arching foliage produces a wide skirt effect below the panicles. The new plant is useful in the landscape as a specimen, en masse, or in a container.

1 Drawing Sheet

Latin botanical classification: *Panicum virgatum* (L.).
Variety denomination: 'Niagara Falls'.

STATEMENT REGARDING PRIOR DISCLOSURES UNDER 37 CFR 1.77(B)(6)

The first non-enabling disclosure of the claimed plant was the photograph and brief description on a website operated by Walters Gardens, Inc. on Dec. 1, 2021. The claimed plant was first sold on May 24, 2021, by Walters Gardens, Inc. to Plant Delights Nursery, Inc. and Overdevest Nurseries. Inc. who obtained the plant and all information relating thereto, from the inventor. No plants of *Panicum* 'Niagara Falls' have been sold in this country or anywhere in the world, nor has any disclosure of the new plant been made more than one year prior to the filing date of this application, and such sale or disclosure within one year was either derived directly or indirectly from the inventor.

BACKGROUND OF THE PLANT

*Panicum* 'Niagara Falls', hereinafter also referred to just by the cultivar name 'Niagara Falls' and the "new plant" is a new and distinct cultivar of Switch Grass.

The new plant originated from a cross by the inventor between 'Apache Rose' U.S. Plant Pat. No. 29,142 and 'Northwind' at a wholesale perennial nursery in Zeeland, Mich. in the late summer of 2014. The seed was collected in the autumn of 2014 and sown the following spring. The individual seedling was initially selected from among many for further observation in the summer and fall of 2016 at which time it was assigned the breeder code 14-5-13 before giving the new plant a cultivar name.

The new plant has been successfully asexually propagated by division since late fall of 2016 at the same wholesale perennial plant nursery in Zeeland, Mich., and found to produce stable and identical plants that maintain the unique characteristics of the original plant. The plant is stable and reproduces true-to-type in successive generations of asexual reproduction.

BRIEF SUMMARY OF THE PLANT

*Panicum* 'Niagara Falls' differs from its female parent, 'Apache Rose', in that the new plant is slightly taller, with more arching foliage, and has more blue-green foliage that does not change over the growing season.

The nearest comparison varieties known to the inventor are: 'Blue Fountain' U.S. Plant Pat. No. 28,192, 'Gunsmoke' U.S. Plant Pat. No. 32,373, 'RR1' U.S. Plant Pat. No. 17,994, 'Northwind' (not patented), 'Shenandoah' (not patented), and 'Thundercloud' U.S. Plant Pat. No. 20,665.

'Blue Fountain' is significantly taller in habit and not as broadly arching. 'Gunsmoke' has a slightly taller habit and is much more upright foliage. 'Northwind' is significantly taller with more upright leaves and the foliage is similar in early leaf color but becomes more yellowish-green in September. 'Shenandoah' is taller and less arching in habit, the culms are looser and not as densely arranged, and the foliage develops a reddish-purple color in the fall. 'Thundercloud' is more than twice as tall, and the habit is less arching with the leaves more outwardly.

Table 1 below includes comparisons of other *Panicum* cultivars known to the inventor:

TABLE 1

| CULTIVAR | U.S. PLANT PAT. NO. | TOTAL HEIGHT (cm) | INITIAL COLOR |
|---|---|---|---|
| 'Apache Rose' | 29,142 | 95 | gray-green |
| 'Bad Hair Day' | 29,313 | 210 | yellow-green |
| 'Blue Fountain' | 28,192 | 210 | blue-green |
| 'Cape Breeze' | 24,895 | 75 | dark green |
| 'Cheyenne Sky' | 23,209 | 112 | blue-green |

TABLE 1-continued

| | | | |
|---|---|---|---|
| 'Dallas Blues' | 11,202 | 193 | grayed blue-green |
| 'Gunsmoke' | 32,373 | 135 | blue-green |
| 'Haense Herms' | (not patented) | 100 | green |
| 'Heavy Metal' | (not patented) | 180 | blue-green |
| 'Hot Rod' | 26,074 | 90 | blue-green |
| 'Niagara Falls' | current appl. | 108 | blue-green |
| 'Northwind' | (not patented) | 180 | blue-green |
| 'Prairie Fire' | 19,367 | 100 | blue-green |
| 'Rostrahlbush' | (not patented) | 110 | green |
| 'RR1' | 17,994 | 120 | blue-green |
| 'Shenandoah' | (not patented) | 140 | blue-green |
| 'Thundercloud' | 20,665 | 275 | blue-green |
| 'Totem Pole' | 29,951 | 200 | blue-green |

| CULTIVAR | SEASONAL COLOR | SEASON OF CHANGE BEGINNING | HABIT |
|---|---|---|---|
| 'Apache Rose' | purple-tipped | late July | dense upright |
| 'Bad Hair Day' | yellow-green | none | upright |
| 'Blue Fountain' | blue-green | none | upright |
| 'Cape Breeze' | purple-tipped | late September | compact upright |
| 'Cheyenne Sky' | concord purple | early July | very upright |
| 'Dallas Blues' | purple-tipped | late September | upright arching |
| 'Gunsmoke' | blue-green | none | arching upright |
| 'Haense Herms' | red-purple | early August | upright |
| 'Heavy Metal' | blue-green | none | very upright |
| 'Hot Rod' | red-purple | early spring | upright |
| 'Niagara Falls' | blue-green | none | upright |
| 'Northwind' | yellow-green | September | upright |
| 'Prairie Fire' | deep wine | early July | upright |
| 'Rostrahlbush' | red-purple | early August | upright |
| 'RR1' | purple-red | early July | compact |
| 'Shenandoah' | red-purple | late July | arching |
| 'Thundercloud' | blue-green | none | arching upright |
| 'Totem Pole' | blue-green | none | columnar |

The new plant has a larger, more-defined, arching skirt than all of the cultivars known to the inventor and in the above Table 1.

The following traits of *Panicum* 'Niagara Falls', in combination, have been repeatedly observed in multiple generations of asexually propagated plants and distinguish the new plant from all other Switch Grass plants known to the inventor:

1. Broad blue-green foliage that retains its coloration into the fall;
2. Upright and dense culms producing medium height plants that do not lodge;
3. Foliage is broadly arching, forming a broad skirt below flowers and seed heads;
4. Broadly-spreading airy panicles beginning greyed reddish-purple and becoming creamy-tan seed heads that are retained into winter.

BRIEF DESCRIPTION OF THE DRAWINGS

The photographs of the new plant demonstrate the overall appearance of a six-year-old plant growing in an outdoor display garden in Zeeland, Mich., including the unique traits. The colors are as accurate as reasonably possible with color reproductions. Ambient light spectrum, source, and direction may cause the appearance of minor variation in color.

DETAILED BOTANICAL DESCRIPTION

Figure 1:
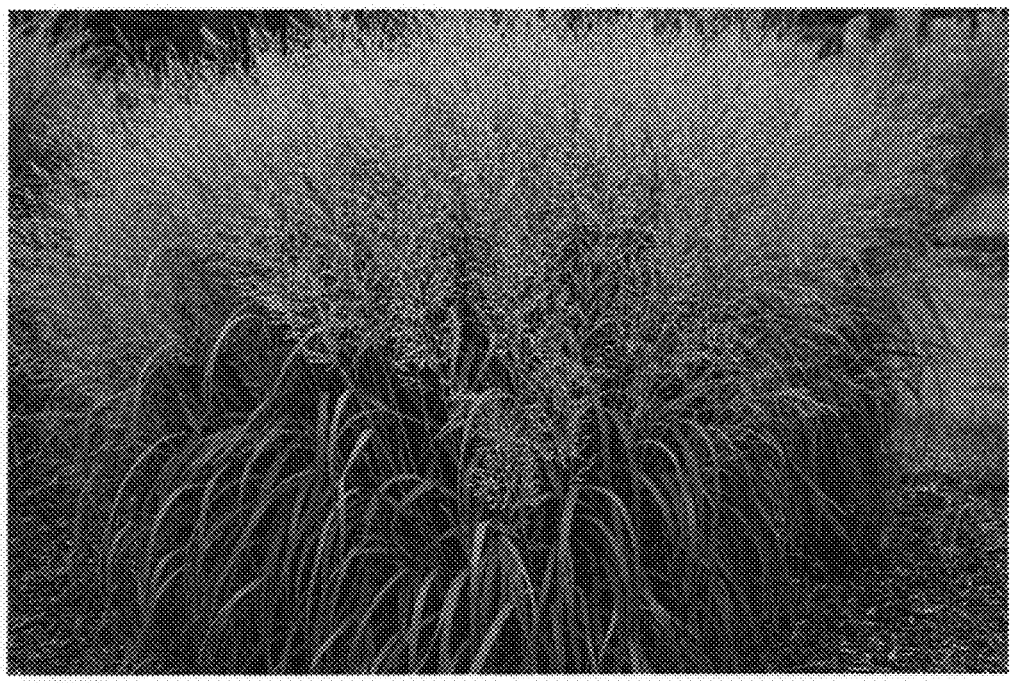
FIG. 1 shows the overall plant in mid-season.
Figure 2:
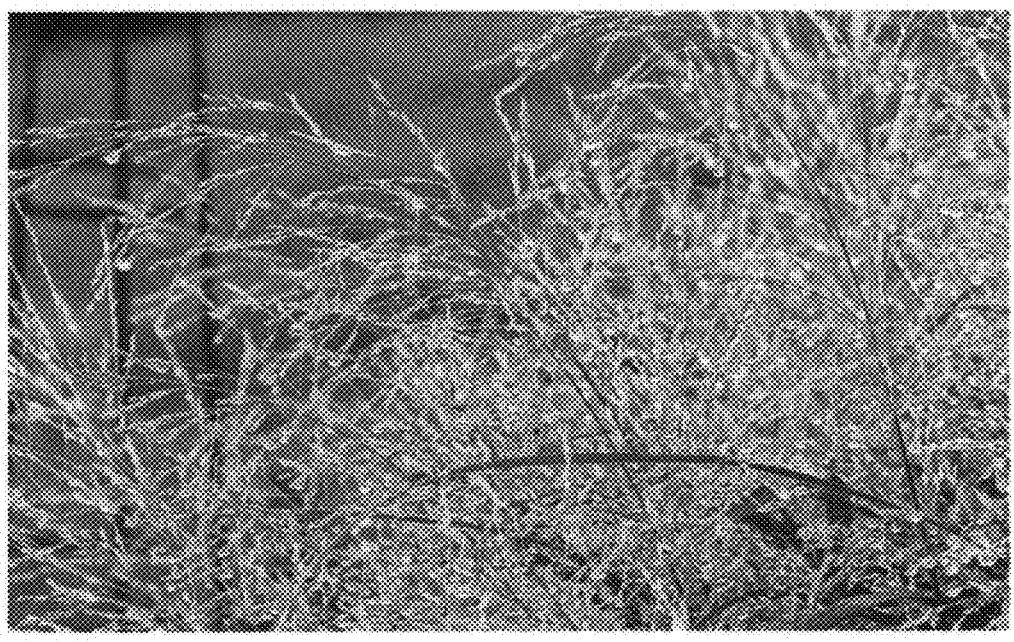
FIG. 2 shows a close-up of the inflorescence in late summer.

The following descriptions and color references are based on the 2015 edition of The Royal Horticultural Society Colour Chart except where common dictionary terms are used. The new plant, 'Niagara Falls', has not been observed in all possible environments. The phenotype may vary slightly with different environmental conditions, such as temperature, light, fertility, moisture, and maturity levels, but without any change in the genotype. The following observations and descriptions are of a six-year-old plant in a loamy-sand trial garden of a wholesale perennial nursery in Zeeland, Mich., USA, grown in full sun with supplemental water and fertilizer as needed.

Parentage: Female (seed parent) 'Apache Rose' times 'Northwind' as the male (pollen parent);

Propagation method: By division of the culms;

Time to finishing in a 3.8-liter pot: Very rapid; about 6 to 8 weeks from 25 mm diameter plug;

Rooting habit: Normal, coarsely branching; root color nearest RHS 155D;

Plant description:

Plant shape and habit: Hardy herbaceous perennial forming tightly, rhizomatous and upright culms with broadly arching foliage, topped with finely-textured airy inflorescence producing a broad clump that is wider than it is tall;

Plant size: Foliage height at flowering time is about 98 cm tall from the soil line to the top of the foliage arch and 108 cm tall to the top of flowers; about 43 cm wide at the soil line and about 134 cm at the widest point about 60 cm above the soil;

Foliage description: Glabrous, glaucous; linear; flat; margin with microscopic marginal dentations; sheathed from the node of attachment to ligule, adaxial and abaxial surfaces dull; strongly arching; deciduous but persist through winter;

Foliage size: To about 74.5 cm long and to about 15 mm wide and about 56.5 cm long without sheath; averaging with sheath about 60 cm long and 11.0 mm wide; shorter at the proximal end; typically 5 leaves per culm;

Foliage color: Adaxial between RHS N138C and RHS 189A; abaxial between RHS N138C and RHS 189B; winter adaxial surface more grey than RHS 164D; winter abaxial surface between RHS 199D and RHS 164D;

Veins: Parallel; midrib about 0.5 mm across; abaxial ridged, adaxial slightly recessed;

Vein color: Adaxial midrib in proximal 5 to 7 cm between RHS 189A and RHS 189B, adaxial secondary veins and abaxial midribs and secondary veins indistinguishable and same color as surrounding leaf;

Culm: Erect; terete, hollow; glabrous; glaucous; dull surface; about 75% enclosed by leaf sheath; about 120 culms per clump;

Culm dimension: To about 67 cm long without panicle, average about 60 cm; to about 4.5 mm diameter at base; internode length average about 13 cm, shorter proximally;

Culm color: Variable; proximally under sheath nearest RHS 145D with an undertone of nearest RHS N138D; midsection nearest RHS 138A without glaucous bloom and with glaucous bloom nearest RHS N138D; distal portion nearest RHS 137B;

Node description: About 5 per culm, slightly swollen to about 5 mm diameter;

Node color: Variable; proximally between RHS 161A and RHS 164C, distally nearest RHS 195A;

Flower description: Finely-branched open panicle, one panicle per culm;

Flower timing: Beginning late August, flowering into September, panicles dry and remain effective through winter; No flower fragrance detected;

Panicle: Ellipsoidal with acute apex; to about 41.0 cm long and 17.0 cm wide near middle; overall effective color variable, nearest RHS 160A to RHS 147C;

Rachis: Terete, branched, glabrous, glaucous; to about 32.0 cm long and about 2.5 mm diameter at base; branches to about 17.5 cm long and about 1.0 mm diameter held at about 70-degree angle above horizontal; color nearest RHS N138B;

Spikelet: Usually with two florets; about 12 mm long;

Rachilla: Thin, terete, stiff; to about 9 mm long and about 0.2 mm diameter; color nearest and RHS N138C;

Lower glume: About 3 mm long and 1 mm wide; without awn; color nearest RHS 186B;

Lemma: Without bristle; acute apex, truncate base; margin entire; upper and lower each about 3 mm long and 0.5 mm wide; color between RHS 139D and RHS 160D;

Palea: Acute apex, truncate base, margin entire; about 2 mm long and 0.7 mm across; translucent, nearest RHS 160D;

Gynoecium: Two;

*Stigma*.—Two, plumose, protruding about 1.5 mm from glume and about 0.5 mm diameter; color nearest RHS 165A.

*Style*.—Thin; about 1 mm long and 0.1 mm diameter; color nearest RHS NN155A.

*Ovary*.—Ellipsoidal; acute apex, rounded base; about 2.5 mm long and 1 mm diameter; color nearest RHS 148B.

Androecium: Two or three;

*Filaments*.—Short; hair-like; up to 1.0 mm long and less than 0.1 mm diameter; color nearest RHS NN155D.

*Anthers*.—Two; dorsifixed, longitudinal; about 2.5 mm long and about 1 mm wide; color nearest RHS N163A.

*Pollen*.—Abundant; less than 0.1 mm in diameter; nearly transparent, color lighter than RHS 155D.

Fruit: Caryopsis; about 2.5 mm long and about 1 mm wide; color between RHS 161D and RHS 199D;

Hardiness: At least from USDA zone 4 through 9;

Growth: The new plant is very drought once established and the stems are resistant to lodging;

Disease and pest resistance or susceptibility: 'Niagara Falls' has superior rust (*Puccinia* sp.) resistance compared to 'Northwinds'. Other disease resistance or susceptibility beyond that typical of other Switch Grasses has not been observed.

I claim:

1. A new and distinct cultivar of ornamental Switch Grass, *Panicum* plant named 'Niagara Falls', as herein described and illustrated.

* * * * *